United States Patent
Sandhu et al.

(10) Patent No.: US 10,743,837 B2
(45) Date of Patent: Aug. 18, 2020

(54) ULTRASOUND WAVEFORM TOMOGRAPHY METHOD AND SYSTEM

(71) Applicant: Delphinus Medical Technologies, Inc., Plymouth, MI (US)

(72) Inventors: Gursharan Singh Sandhu, Plymouth, MI (US); Cuiping Li, Plymouth, MI (US); Olivier Roy, Plymouth, MI (US); Steven Schmidt, Plymouth, MI (US); Nebojsa Duric, Plymouth, MI (US)

(73) Assignee: Delphinus Medical Technologies, Inc., Novi, MI (US)

( * ) Notice: Subject to any disclaimer, the term of this patent is extended or adjusted under 35 U.S.C. 154(b) by 1150 days.

(21) Appl. No.: 14/817,470

(22) Filed: Aug. 4, 2015

(65) Prior Publication Data
US 2016/0030000 A1    Feb. 4, 2016

Related U.S. Application Data

(60) Provisional application No. 62/032,939, filed on Aug. 4, 2014, provisional application No. 62/094,774, filed
(Continued)

(51) Int. Cl.
*A61B 8/15* (2006.01)
*A61B 8/00* (2006.01)
(Continued)

(52) U.S. Cl.
CPC .............. *A61B 8/15* (2013.01); *A61B 8/0825* (2013.01); *A61B 8/4494* (2013.01);
(Continued)

(58) Field of Classification Search
USPC ......................................................... 600/448
See application file for complete search history.

(56) References Cited

U.S. PATENT DOCUMENTS

| 3,154,067 A | 10/1964 | Stenstrom et al. |
| 3,881,466 A | 5/1975 | Wilcox |

(Continued)

FOREIGN PATENT DOCUMENTS

| AU | 3443295 A | 5/1996 |
| EP | 284055 A | 9/1988 |

(Continued)

OTHER PUBLICATIONS

Kim et al. ("Analysis of inverse scattering solution from single frequency, combined transmission and reflection data for the Helmholtz and Riccati exact wave equations"; Acoustical imaging; pp. 359-369, vol. 15).*

(Continued)

*Primary Examiner* — Bill Thomson
*Assistant Examiner* — Shahdeep Mohammed
(74) *Attorney, Agent, or Firm* — Wilson Sonsini Goodrich & Rosati

(57) ABSTRACT

A method and system for generating an enhanced image of a volume of tissue, the method comprising: emitting acoustic waveforms toward the volume of tissue; detecting a set of acoustic signals derived from acoustic waveforms interacting with the volume of tissue; generating, from the set of acoustic signals, an initial model representing a distribution of an acoustomechanical parameter across a region of the volume of tissue; extracting a set of frequency components, from the set of acoustic signals; generating a first simulated wavefield with a first frequency component of the set of frequency components; generating an updated model of the initial model with the first simulated wavefield; iteratively refining the updated model with a set of simulated wavefields associated with the set of frequency components until a threshold condition is satisfied, thereby producing a final
(Continued)

model; and generating the enhanced image from the final model of the volume of tissue.

22 Claims, 6 Drawing Sheets

Related U.S. Application Data on Dec. 19, 2014, provisional application No. 62/109,370, filed on Jan. 29, 2015.

(51) Int. Cl.
*A61B 8/08* (2006.01)
*G06T 11/00* (2006.01)

(52) U.S. Cl.
CPC .......... *A61B 8/5207* (2013.01); *G06T 11/006* (2013.01); *G06T 2211/424* (2013.01)

(56) References Cited

U.S. PATENT DOCUMENTS

| | | | |
|---|---|---|---|
| 3,886,489 A | 5/1975 | Jones |
| 4,028,934 A | 6/1977 | Sollish |
| 4,059,010 A | 11/1977 | Sachs |
| 4,363,326 A | 12/1982 | Kopel |
| 4,412,288 A | 10/1983 | Herman |
| 4,481,948 A | 11/1984 | Sole |
| 4,515,165 A | 5/1985 | Carroll |
| 4,542,744 A | 9/1985 | Barnes et al. |
| 4,564,019 A | 1/1986 | Miwa |
| 4,606,342 A | 8/1986 | Zamba et al. |
| 4,671,256 A | 6/1987 | Lemelson |
| 4,858,124 A | 8/1989 | Lizzi et al. |
| 4,917,096 A | 4/1990 | Englehart et al. |
| 5,025,792 A | 6/1991 | Hon et al. |
| 5,029,476 A | 7/1991 | Metala et al. |
| RE33,672 E | 8/1991 | Miwa |
| 5,103,129 A | 4/1992 | Slayton et al. |
| 5,143,069 A | 9/1992 | Kwon et al. |
| 5,158,071 A | 10/1992 | Umemura et al. |
| 5,158,536 A | 10/1992 | Sekins et al. |
| 5,179,455 A | 1/1993 | Garlick |
| 5,212,571 A | 5/1993 | Garlick et al. |
| 5,255,683 A | 10/1993 | Monaghan |
| 5,267,566 A | 12/1993 | Choucair et al. |
| 5,269,309 A | 12/1993 | Fort et al. |
| 5,280,788 A | 1/1994 | Janes et al. |
| 5,297,553 A | 3/1994 | Sliwa et al. |
| 5,304,173 A | 4/1994 | Kittrell et al. |
| 5,318,028 A | 6/1994 | Mitchell et al. |
| 5,329,817 A | 7/1994 | Garlick et al. |
| 5,349,954 A | 9/1994 | Tiemann et al. |
| 5,372,138 A | 12/1994 | Crowley et al. |
| 5,413,108 A | 5/1995 | Alfano |
| 5,415,164 A | 5/1995 | Faupel et al. |
| 5,421,338 A | 6/1995 | Crowley et al. |
| 5,433,202 A | 7/1995 | Mitchell et al. |
| 5,463,548 A | 10/1995 | Asada et al. |
| 5,465,722 A | 11/1995 | Fort et al. |
| 5,474,072 A | 12/1995 | Shmulewitz |
| 5,479,927 A | 1/1996 | Shmulewitz |
| 5,485,839 A | 1/1996 | Aida et al. |
| 5,487,387 A | 1/1996 | Trahey et al. |
| 5,492,126 A | 2/1996 | Hennige et al. |
| 5,513,639 A | 5/1996 | Satomi et al. |
| 5,524,630 A | 6/1996 | Crowley |
| 5,558,092 A | 9/1996 | Unger et al. |
| 5,573,497 A | 11/1996 | Chapelon |
| 5,582,173 A | 12/1996 | Li |
| 5,590,653 A | 1/1997 | Aida et al. |
| 5,590,657 A | 1/1997 | Cain et al. |
| 5,596,992 A | 1/1997 | Haaland et al. |
| 5,606,971 A | 3/1997 | Sarvazyan |
| 5,620,479 A | 4/1997 | Diederich |
| 5,640,956 A | 6/1997 | Getzinger et al. |
| 5,660,185 A | 8/1997 | Shmulewitz et al. |
| 5,664,573 A | 9/1997 | Shmulewitz |
| 5,673,698 A | 10/1997 | Okada et al. |
| 5,678,565 A | 10/1997 | Sarvazyan |
| 5,715,825 A | 2/1998 | Crowley |
| 5,743,863 A | 4/1998 | Chapelon |
| 5,762,066 A | 6/1998 | Law et al. |
| 5,766,129 A | 6/1998 | Mochizuki |
| 5,785,663 A | 7/1998 | Sarvazyan |
| 5,797,849 A | 8/1998 | Vesely et al. |
| 5,800,350 A | 9/1998 | Coppleson et al. |
| 5,810,731 A | 9/1998 | Sarvazyan et al. |
| 5,817,025 A | 10/1998 | Alekseev et al. |
| 5,830,133 A | 11/1998 | Osten et al. |
| 5,833,614 A | 11/1998 | Dodd et al. |
| 5,833,627 A | 11/1998 | Shmulewitz et al. |
| 5,833,633 A | 11/1998 | Sarvazyan |
| 5,836,882 A | 11/1998 | Frazin |
| 5,836,894 A | 11/1998 | Sarvazyan |
| 5,846,202 A | 12/1998 | Ramamurthy et al. |
| 5,851,182 A | 12/1998 | Sahadevan |
| 5,865,167 A | 2/1999 | Godik |
| 5,865,743 A | 2/1999 | Godik |
| 5,891,619 A | 4/1999 | Zakim et al. |
| 5,945,674 A | 8/1999 | Dukor |
| 6,002,958 A | 12/1999 | Godik |
| 6,014,473 A | 1/2000 | Hossack et al. |
| 6,109,270 A | 8/2000 | Mah et al. |
| 6,117,080 A | 9/2000 | Schwartz |
| 6,146,897 A | 11/2000 | Cohenford et al. |
| 6,165,734 A | 12/2000 | Garini et al. |
| 6,245,017 B1 | 6/2001 | Hashimoto et al. |
| 6,256,090 B1 | 7/2001 | Chen et al. |
| 6,351,660 B1 | 2/2002 | Burke et al. |
| 6,385,474 B1 | 5/2002 | Rather et al. |
| 6,428,477 B1 | 8/2002 | Mason |
| 6,451,013 B1 | 9/2002 | Bays et al. |
| 6,574,499 B1 | 6/2003 | Dines et al. |
| 6,612,988 B2 | 9/2003 | Maor et al. |
| 8,532,951 B2 | 9/2013 | Roy et al. |
| 8,663,113 B2 | 3/2014 | Schmidt et al. |
| 8,870,771 B2 | 10/2014 | Glide-Hurst et al. |
| 8,876,716 B2 | 11/2014 | Duric et al. |
| 9,113,835 B2 | 8/2015 | Li |
| 2001/0051774 A1 | 12/2001 | Littrup et al. |
| 2004/0122325 A1 | 6/2004 | Chambers et al. |
| 2004/0152986 A1 | 8/2004 | Fidel et al. |
| 2005/0165309 A1 | 7/2005 | Varghese et al. |
| 2006/0084859 A1 | 4/2006 | Johnson et al. |
| 2007/0015949 A1 | 1/2007 | Kaiser |
| 2007/0167823 A1 | 7/2007 | Lee et al. |
| 2007/0282200 A1 | 12/2007 | Johnson et al. |
| 2008/0058682 A1 | 3/2008 | Azhari et al. |
| 2008/0103393 A1* | 5/2008 | Specht .............. A61B 8/42 600/437 |
| 2008/0229832 A1 | 9/2008 | Huang et al. |
| 2009/0076379 A1 | 3/2009 | Hamill et al. |
| 2009/0129556 A1 | 5/2009 | Ahn |
| 2011/0146371 A1* | 6/2011 | Roy .............. A61B 8/0825 73/1.79 |
| 2011/0152685 A1 | 6/2011 | Misono |
| 2011/0201932 A1 | 8/2011 | Duric et al. |
| 2012/0283566 A1 | 11/2012 | Li |
| 2013/0041261 A1* | 2/2013 | Li .............. A61B 8/15 600/442 |
| 2013/0204137 A1 | 8/2013 | Roy et al. |
| 2013/0267850 A1 | 10/2013 | Berman |
| 2014/0276068 A1 | 9/2014 | Szpak et al. |
| 2014/0316269 A1 | 10/2014 | Zhang et al. |
| 2014/0364736 A1* | 12/2014 | Huang .............. A61B 8/13 600/447 |
| 2015/0313577 A1 | 11/2015 | Duric et al. |

FOREIGN PATENT DOCUMENTS

| | | |
|---|---|---|
| EP | 317049 A | 5/1989 |
| EP | 320444 A | 6/1989 |

(56) References Cited

FOREIGN PATENT DOCUMENTS

| EP | 351610 | A | 1/1990 |
|---|---|---|---|
| EP | 538241 | A | 4/1993 |
| EP | 0609922 | A | 8/1994 |
| EP | 614651 | A | 9/1994 |
| EP | 642762 | A | 3/1995 |
| EP | 661029 | A | 7/1995 |
| EP | 774276 | A | 5/1997 |
| WO | 199947046 | | 9/1999 |

OTHER PUBLICATIONS

Dessa et al. ("combined traveltime and frequency-domain seismic waveform inversion: a case study on multi-offset ultrasonic data"; Geophys. J. Int. (2003) 154, 117-133).*
Andre et al., "A New Consideration of Diffraction Computed Tomography for Breast Imaging: Studies in Phantoms and Patients," Acoustical Imaging, 21, 379 (1995).
Candy et al., "Signal Processing: The Model-Based Approach," pp. 178-213 (McGraw Hill, 1986).
Chelfouh et al., "Characterization of Urinary Calculi: in Vitro Study of 'Twinking Artifact' revealed by Color-Flow Sonography," AJR Am. J. Roentgenol. 171( 4) (1998) 1055-60.
Greenleaf et al., "Multidimensional Visualization of Ultrasonic Images," J Acoust Soc Amer 95 (1994) 2902.
Greenleaf et al., "Introduction to Computer Ultrasound Tomography," Computer Aided Tomography and Ultrasonics in Medicine, (1970) North-Holland 125-136.
Harmuth, "Sequency Theory: Foundations and Applications, Advances in Electronics and Electron Physics," (Academic Press, 1977) 18-95.
Haykin, "Neural Networks—A Comprehensive Foundation," Prentice Hall (1998) 236-284.
Hebden et al., "Acoustically Modulated Electrical Impedance Tomography,"Proc SPIE 1231 (1990) 7-14.
Jellins, "Breast Tissue Characterization" Tissue Characterization with Ultrasound 2 (1986) CRC Press 95-122.
Louvar et al., "Correlation of Color Doppler Flow in the Prostate with Tissue Microvascularity," Cancer 1:83(1) (1998) 135-40.
Mitchell, An Introduction to Genetic Algorithms, pp. 8-11, 35-78, 155-179 (MIT Press, 1996).
Nelson et al., "Interactive Acquisition, Analysis and Visualization of Sonographic Volume Data," International J Imaging Sys and Tech 8(26) (1997) 26-37.
Sehgal et al., "Visualization of Breast Calcification by Acoustic Resonance Imaging," Radiology Supplement, 84th Scientific Assembly and Annual Meeting, Nov. 29-Dec. 4, 1998 presented in McCormick Place, Chicago, Illinois, vol. 209, listing: 1150 (1998).
Shi et al., "Effects of Pressure Changes on Harmonic and Subharmonic Response of US Contrast Microbubbles," 84th Scientific Assembly and Annual Meeting, Nov. 29-Dec. 4, 1998, presented in McCormick Place, Chicago, Illinois, vol. 209, listing: 1154 (1998).
Chang et al., Kirchhoff migration of ultrasonic images, Materials evaluation, V59, N3, 413-417, 2001.
Klimes, Grid Travel-time Tracing: Second-order Method for the First Arrivals in Smooth Media, PAGEOPH, vol. 148, Nos. 3/4, 1996.
Li et al., Breast Imaging Using Transmission Ultrasound: Reconstructing Tissue Parameters of Sound Speed and Attenuation,2008 International Conference on BioMedical Engineering and Informatics, IEEE computer society, 708-712.
Li et al., Comparison of ultrasound attenuation tomography methods for breast imaging, Medical Imaging 2008: UltrasonicImaging and Signal Processing, Proc. of SPIE vol. 6920, 692015-(1-9), 2008.
Li et al., Refraction corrected transmission ultrasound computed tomography for application in breast imaging, Med. Phys. 37(5), May 2010, 2233-2246.
Schmidt et al., "Modification of Kirchhoff migration with variable sound speed and attenuation for tomographic imaging of the breast," Proc. of SPIE vol. 7968, Mar. 25, 2011.
Walach et al., Local Tissue Attenuation Images Based on Pulsed-Echo Ultrasound Scans, IEEE Transactions Onbiomedical Engineering, vol. 36. No. 2, Feb. 1989.

* cited by examiner

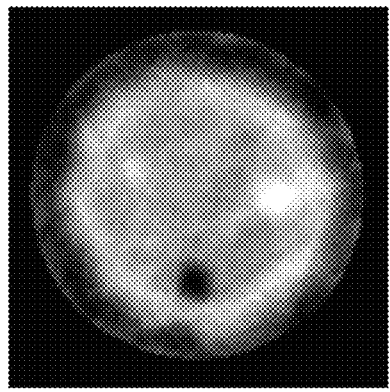 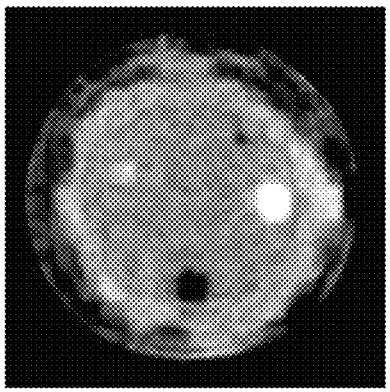 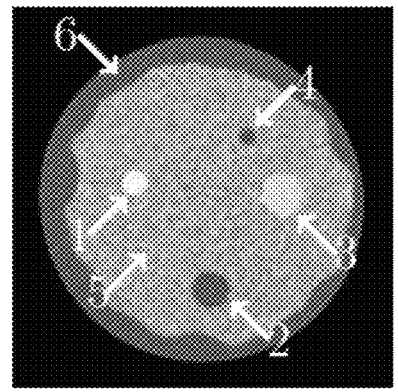
FIGURE 7A  FIGURE 7B  FIGURE 7C
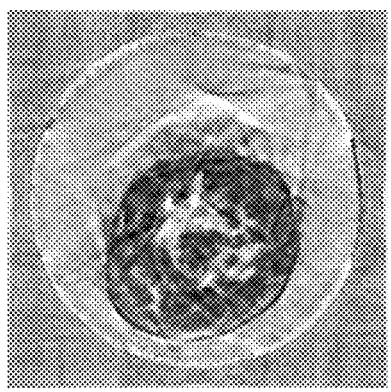 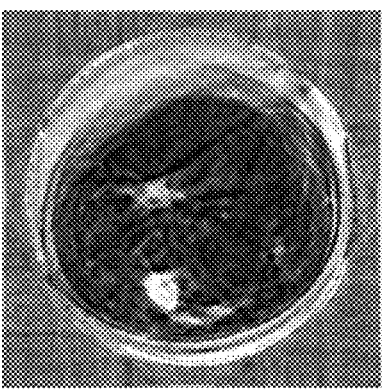 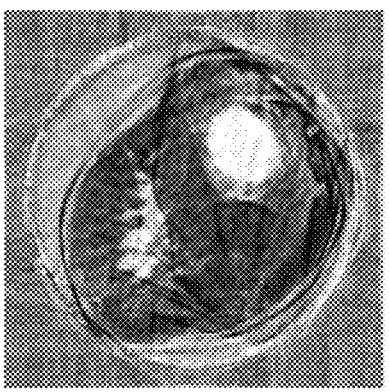
FIGURE 8A  FIGURE 8B  FIGURE 8C
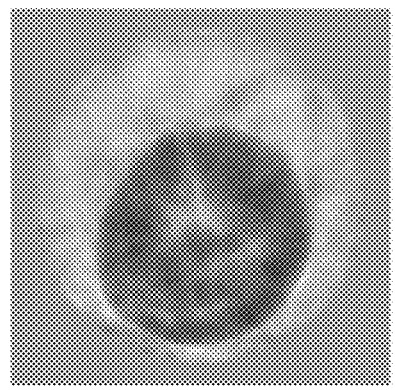 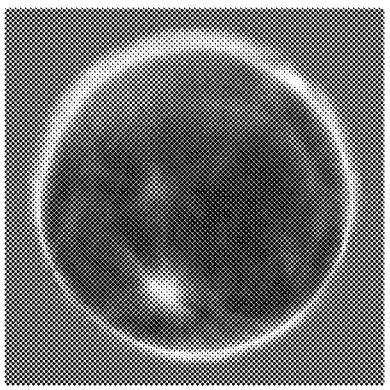 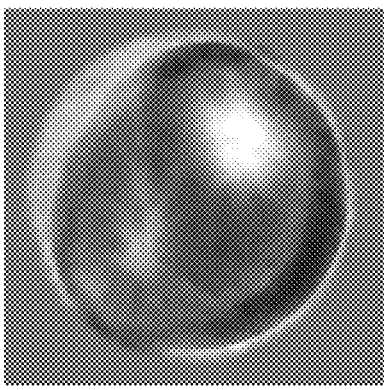
FIGURE 8D  FIGURE 8E  FIGURE 8F

ULTRASOUND WAVEFORM TOMOGRAPHY METHOD AND SYSTEM

CROSS-REFERENCE TO RELATED APPLICATIONS

This application claims the benefit of U.S. Provisional Application Ser. No. 62/032,939, filed on 4 Aug. 2014, U.S. Provisional Application Ser. No. 62/094,774, filed on 19 Dec. 2014, and U.S. Provisional Application Ser. No. 62/109,370, filed on 29 Jan. 2015, which are each incorporated herein in its entirety by this reference.

TECHNICAL FIELD

This invention relates generally to the medical imaging field, and more specifically to an improved ultrasound waveform tomography method and system in the ultrasound medical imaging field.

BACKGROUND

Early detection of breast cancer and other types of cancer is typically an important factor in successful treatment. Ultrasound tomography is a promising imaging modality that has the potential to improve medical imaging of tissue for screening and diagnosis purposes compared to conventional imaging techniques. For instance, mammography is the current standard for breast screening, but involves ionizing radiation that precludes frequent imaging, and mammography has low sensitivity for detection of cancer in patients with dense breast tissue, which leads to a relatively high false negative rate. As another example, magnetic resonance imaging (MRI) is prohibitively expensive for routine use and also has limited accessibility.

A basic principle of conventional ultrasound involves emitting an acoustic wave or beam along a focused path from a source transmitter, and allowing the wave to scatter (e.g., in reflection, refraction, diffraction, transmission) from tissue or other boundaries in its path. The scattered wave returns to a surface of one or more receiving elements, which can be centered around and/or include the transmitter(s). The time of travel can be converted into a depth distance by multiplying the time by an assumed speed of sound in the media. The received signal is then output to a graphical display for user interpretation. Image reconstruction methods used by current ultrasound systems are, however, limited by the wavelength of ultrasound used, and typically fail when the characteristic dimension of a lesion is similar in dimension or smaller than the wavelength of ultrasound used. Additionally, current ultrasound systems and methods are typically configured to accommodate a small imaging region, resulting in difficulties in imaging and characterizing entire organs, such as the breast. As an additional factor, measurement of tissue parameters and provision of analyses derived from such measurement are limited in current systems due to deficiencies in current ultrasound systems and methods for generating and processing signals. Furthermore, the performance of ultrasound scanning is dependent on the skills of the operator and image quality can vary from user to user.

Thus, there is a need in the ultrasound imaging field to create an improved ultrasound waveform tomography method and system. This invention provides such an improved method and system.

BRIEF DESCRIPTION OF THE FIGURES

FIGS. 7A-7C depict an example enhanced image and comparison images associated with and embodiment of an ultrasound waveform tomography method;

FIGS. 8A-8C depict example enhanced images generated according to an example of an ultrasound waveform tomography method; and FIGS. 8D-8F depict example images reconstructed using a travel time tomography method, for comparison.

DESCRIPTION OF THE PREFERRED EMBODIMENTS

The following description of preferred embodiments of the invention is not intended to limit the invention to these preferred embodiments, but rather to enable any person skilled in the art to make and use this invention.

1. Method

Figure 1:
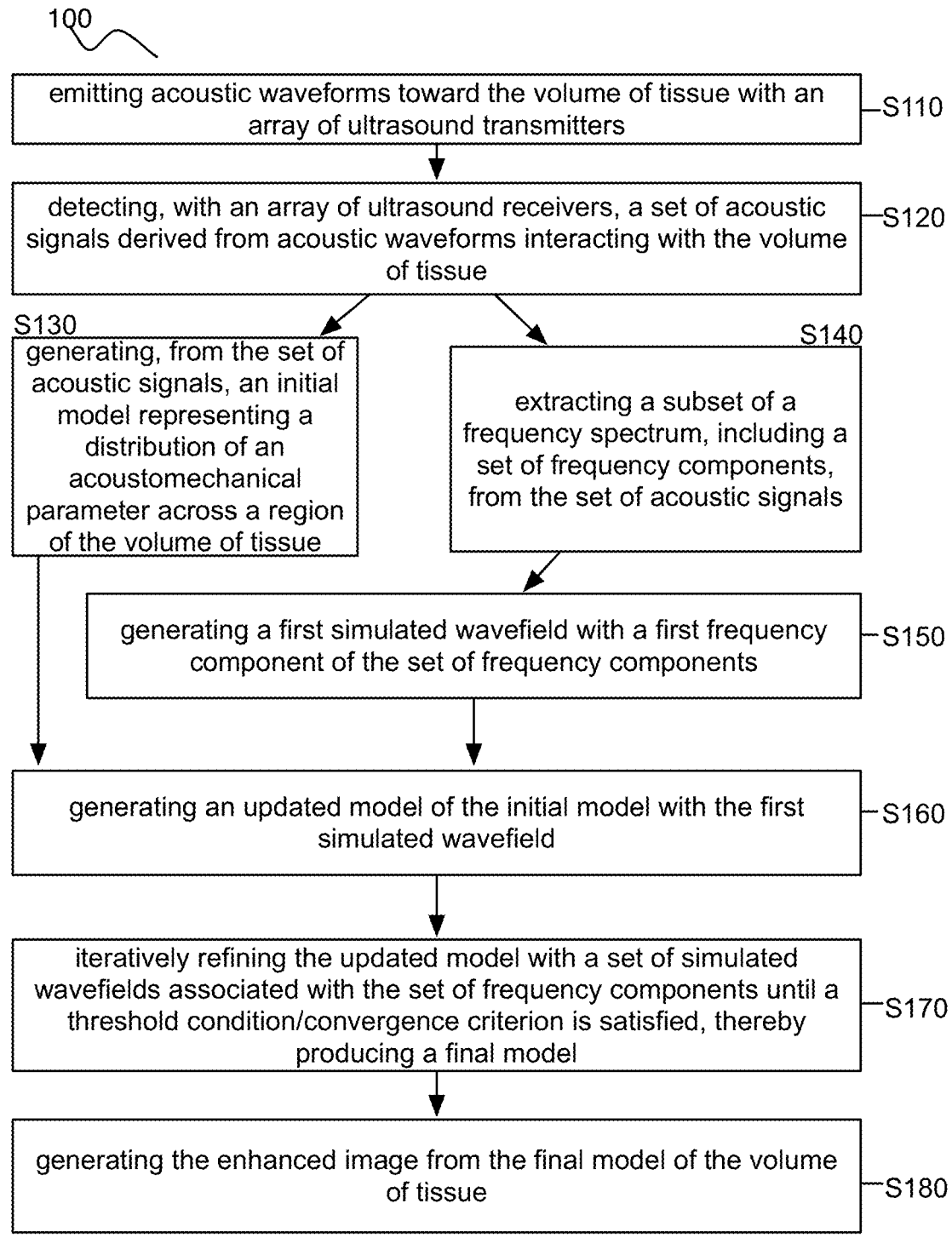
FIG. 1 is a schematic flowchart of an ultrasound waveform tomography method.

In one embodiment, as shown in FIG. 1, a method 100 for generating an enhanced image of a volume of tissue includes: emitting acoustic waveforms toward the volume of tissue with an array of ultrasound transmitters S110; detecting, with an array of ultrasound receivers, a set of acoustic signals S120 derived from acoustic waveforms interacting with the volume of tissue; generating, from the set of acoustic signals, an initial model representing a distribution of an acoustomechanical parameter across a region of the volume of tissue S130; extracting a subset of a frequency spectrum, including a set of frequency components, from the set of acoustic signals S140; generating a first simulated wavefield with a first frequency component of the set of frequency components S150; generating an updated model of the initial model with the first simulated wavefield S160; iteratively refining the updated model with a set of simulated wavefields associated with the set of frequency components until a threshold condition is satisfied, thereby producing a final model S170; and generating the enhanced image from the final model of the volume of tissue S180.

The method 100 functions to render ultrasound images and/or generate transformed ultrasound data that can be used to generate high-resolution images of a volume of tissue (e.g., breast tissue), to aid in the detection and diagnosis of cancer and other pathologies. The method 100 can further function to enable detection of tissue pathologies that have characteristic dimensions that are similar in size to or smaller than a characteristic of wavelength of ultrasound used. In providing higher-resolution images, the method 100 preferably implements waveform tomography reconstruction algorithms that model the propagating wavefields using the full wave equation, thereby taking into account higher order effects (e.g., diffraction, multiple scattering, etc.). Current travel time tomography techniques, in contrast, only consider arrival times of transmitted wavefronts, which limits consideration of higher order effects. The method 100 also preferably omits an assumption of a homogeneous background in a tissue volume of interest, thus enabling the method 100 to have utility in relation to characterization of tissue masses within heterogeneous tissues. The method 100 is preferably fully automated, such that a user does not need to provide any input in implementation of the waveform tomography reconstruction algorithm implemented by the method 100; however, in some alternative variations, at least some portions of the method 100 can be semi-automated or manual, with involvement of a user.

In some embodiments, the method 100 can function to produce images that are aligned with regulatory standards for medical imaging, as regulated, for instance, by the U.S. Food and Drug Administration (FDA). In relation to pathogenic masses, the method 100 can provide significant improvements over currently available methods and systems (e.g., mammographic methods and systems), in particular, for dense tissues. In relation to current ultrasound methods and systems, the method 100 can improve sensitivity in detection of suspicious masses, while providing specificity in characterization of types of masses (e.g., in comparison to reflection ultrasound alone). The method 100 can, however, function to enable diagnosis, monitoring, and/or characterization of a volume of tissue in any other suitable manner.

In one embodiment, the method 100 is used to generate one or more renderings of regions of a volume of tissue that can be used to detect abnormalities (e.g., cancerous tissues) in a human or other animal. In a specific application, the method 100 and system 200 can be used to facilitate detection and diagnosis of early stage breast cancer in breasts of different densities (e.g., fatty breasts, dense breasts, etc.), with improved structural margins that enable differentiation between benign and malignant masses including tumors (e.g., high sound speed tumors), parenchymas, and cysts. Furthermore, in the specific application, the method 100 and system can provide improvements in contrast and resolution over current ray-based methods of reconstructing ultrasound images, in particular for enabling pathology detection within dense tissues. However, the method 100 can be used in any suitable application for imaging a volume of tissue or other suitable object. The method 100 is preferably implemented, at least in part, by way of an embodiment, variation, and/or example of the system 200 described in Section 2 below; however, the method 100 can additionally or alternatively be implemented using any other suitable system.

1.1 Method—Emitting and Receiving Signals

Block S110 recites: emitting acoustic waveforms toward the volume of tissue with an array of ultrasound transmitters, and Block S120 recites: detecting, with an array of ultrasound receivers, a set of acoustic signals derived from acoustic waveforms interacting with the volume of tissue. Blocks S110 and S120 function to gather acoustic data from which renderings of the volume of tissue can be derived in other Blocks of the method 100. Emitting acoustic waveforms preferably includes surrounding the volume of tissue with the array of ultrasound transmitters, and more preferably with a ring transducer comprising the array of ultrasound transmitters, wherein the ring transducer is configured to surround the volume of tissue with the array of ultrasound transmitters. The acoustic waveforms can be characterized by frequencies of approximately 1-20 MHz, or any suitable frequency for medical imaging or other applications. The detected acoustic signals of Block S120 are preferably derived from interactions between the emitted acoustic waveforms of Block S110 and the tissue, wherein interactions can include one or more of: scattering (e.g., reflection, refraction, diffraction, diffusion, etc.) and transmission of the acoustic waves through the tissue. In more detail, scattered acoustic signals can be used to provide reflection data (e.g., B-Mode data) associated with impedance properties of the volume of tissue, and transmitted acoustic waves can be used to provide sound speed and attenuation data associated with the volume of tissue. The acoustic signals can travel along a straight, bent, zig-zag, or curved path, or a path of any suitable shape as determined by the physics of acoustic wave propagation.

Figure 2A:
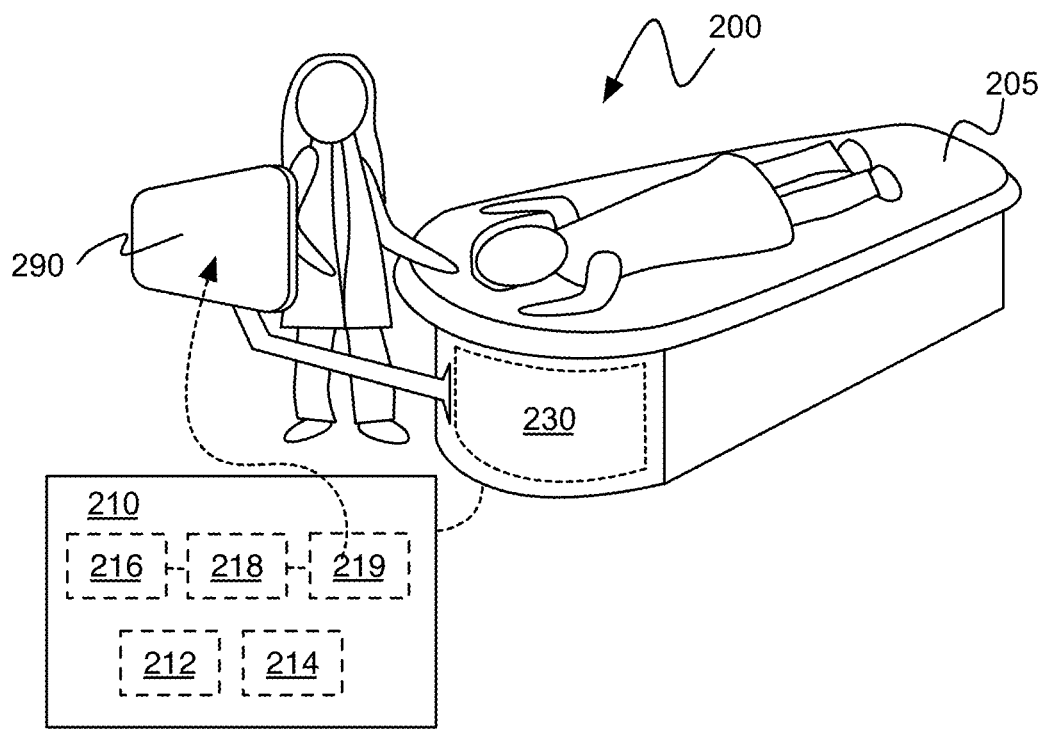
FIGS. 2A-2C depict portions of an embodiment of a system for implementing an embodiment of an ultrasound waveform tomography method.

In Blocks S110 and S120, emitting acoustic waveforms and detecting a set of acoustic signals can be performed with an ultrasound tomographic scanner 200 and methods similar to those described in U.S. Pat. Nos. 6,385,474 and 8,663,113, and U.S. Publication Nos. 2011/0201932 and 2013/0041261, which are each incorporated in its entirety by this reference. However, any suitable ultrasound device or scanner may be used. As shown in FIG. 2A, the steps of scanning the tissue and detecting acoustic signals are preferably performed during a scan of a patient lying prone on their stomach on a scanner table 205 having an opening that provides access to the volume of tissue of the patient. The table, which may be made of a durable, flexible material (e.g., flexible membrane, fabric, etc.), preferably contours to the patient's body, thereby increasing scanning access to the axilla regions of the breast and increasing patient comfort. The opening in the table allows the breast (or other appendage) to protrude through the table and be submerged in an imaging tank 230 filled with water or another suitable fluid as an acoustic coupling medium that propagates acoustic waves.

Figure 2B:
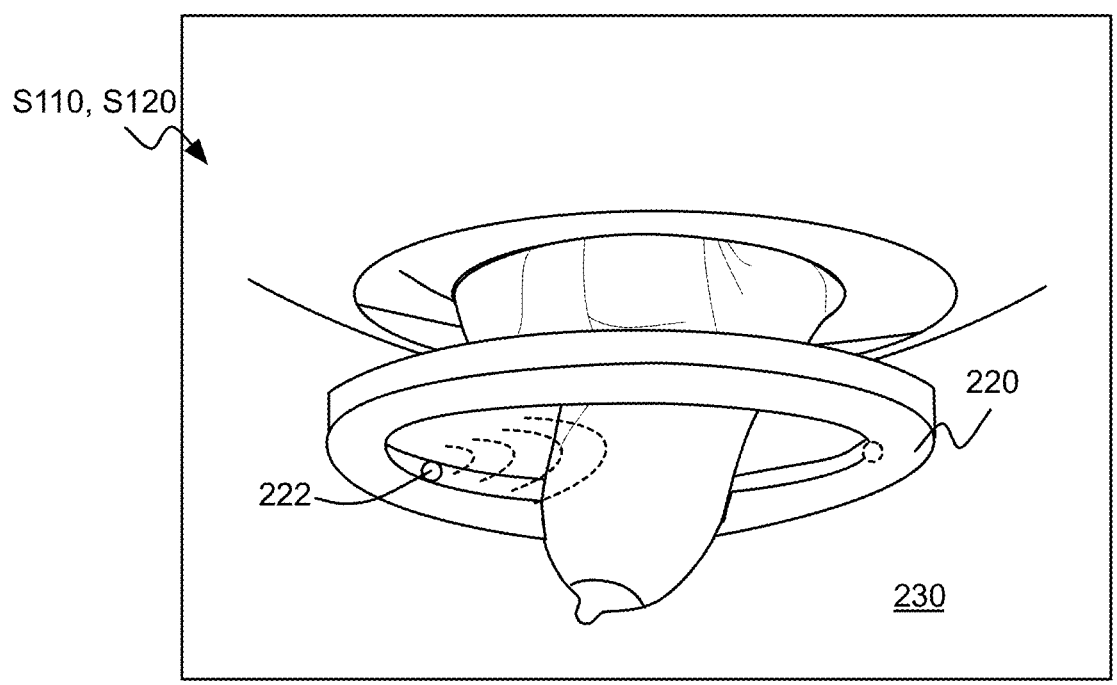
Figure 2C:
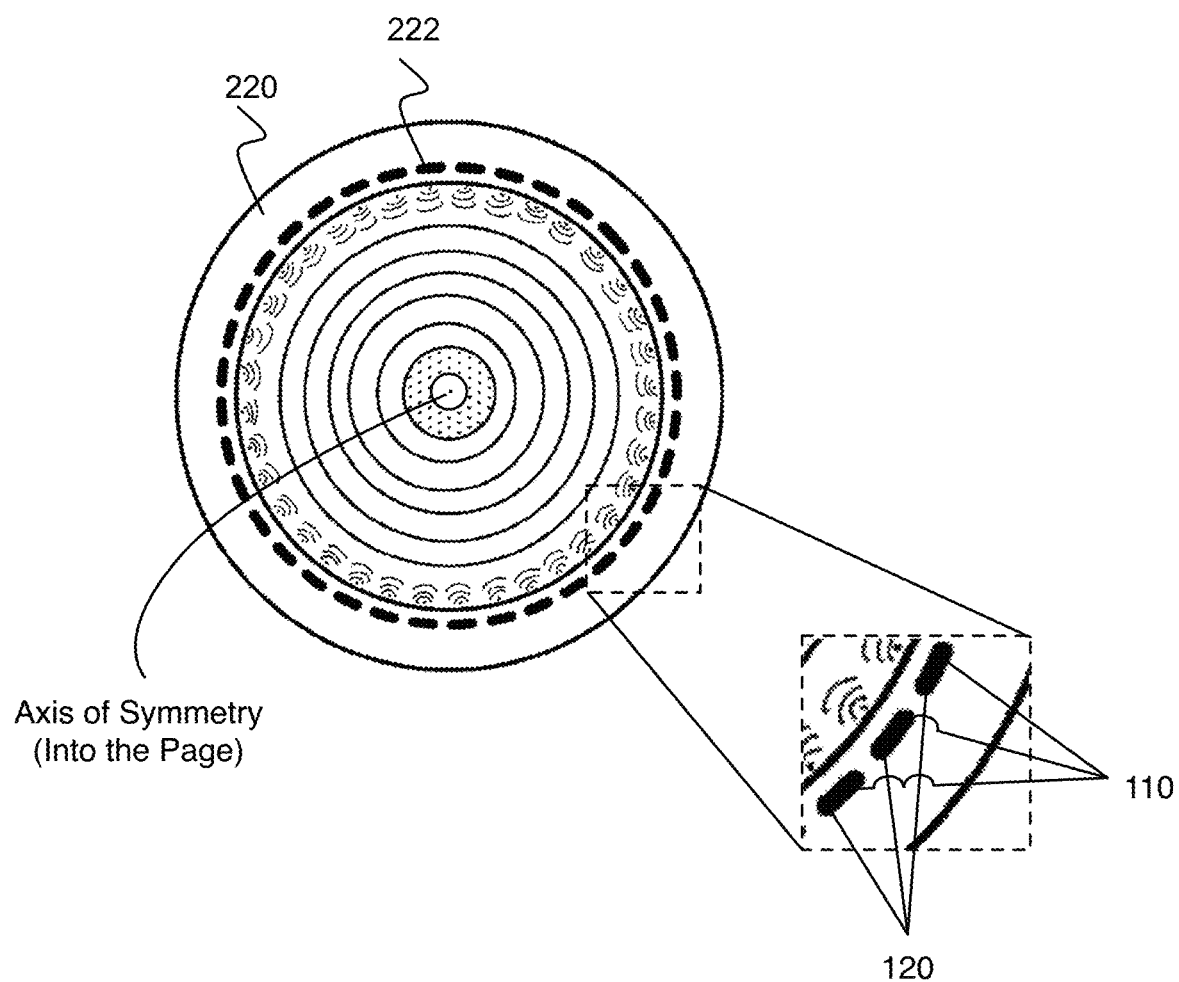

As shown in FIGS. 2B and 2C, a ring-shaped transducer 220 with transducer elements 222 can be located within the imaging tank and encircle or otherwise surround the breast, wherein the transducer elements 222 can comprise an array of ultrasound transmitters 110 and/or an array of ultrasound receivers 120. Multiple ultrasound transmitters 110 that direct safe, non-ionizing ultrasound pulses toward the tissue, and multiple ultrasound receivers 120 that receive and record acoustic signals scattering from the tissue and/or transmitted through the tissue, are distributed around the ring transducer 220, and in one configuration, can be organized such that each ultrasound transmitter element is paired with a corresponding ultrasound receiver element, each ultrasound transmitter element is surrounded by two adjacent ultrasound transmitter elements, each ultrasound receiver element is surrounded by two adjacent ultrasound receiver elements, and the transducer is axially symmetric, as in FIG. 2C. During the scan, the ring transducer 220 moves to image all of the targeted tissue, such as in an anterior-posterior direction between the chest wall and the nipple region of the breast to acquire an acoustic data set including measurements such as acoustic reflection, acoustic attenuation, and sound speed, preferably at discrete scanning steps, or coronal "slices". The ring transducer 220 can be configured to scan step-wise in increments or travel continuously from the chest wall towards the nipple, and/or from the nipple towards the chest wall. However, the ring transducer 220 may additionally and/or alternatively receive data regarding any suitable biomechanical property of the tissue during the scan, and in any suitable direction.

In some embodiments, the scanner table can comprise an embodiment, variation, or example of the patient interface system described in U.S. application Ser. No. 14/208,181 entitled "Patient Interface System" and filed on 13 Mar. 2014 and/or U.S. application Ser. No. 14/811,316 entitled "System for Providing Scanning Medium" and filed on 28

Jul. 2015, which are each hereby incorporated in its entirety by this reference. In a specific example, Blocks S110 and/or S120 can implement a ring transducer 220 having 2048 transducer elements in cooperation with an ultrasound tomographic scanner 200 having 512 receive channels, 512 transmit channels, an operating frequency of 3 MHz and a signal bandwidth centered at 2.5 MHz, a data resolution of 14 bits, an image resolution of 0.7 mm, a slice thickness of 2.5 mm, a reconstruction time per slice of 15 seconds, and an ability to accommodate volumes of tissue 22 cm in diameter. In another specific example, Blocks S110 and/or S120 can implement a ring transducer 220 having a 100 mm radius with 256 transducer elements radially distributed about a center point of the transducer 220, and a signal bandwidth centered at 1.5 MHz. However, Blocks S110 and/or S120 can additionally or alternatively be implemented using any other suitable patient interface system.

Emitting and detecting in Blocks S110 and S120 are preferably performed in a rapid manner, such as with a data acquisition time of less than approximately 1 second per "slice", which may help to avoid motion artifacts in the subsequent morphology renderings and enables the use of contrast agents. However, any other suitable acquisition time can characterize emitting acoustic waveforms and/or detecting acoustic signals as in Blocks S110 and S120. The emitted waveforms and/or detected signals can additionally or alternatively be beamformed on a transducing element. In some embodiments, however, Blocks S110 and/or S120 of the method 100 can, however, additionally and/or alternatively include retrieving acoustic signals from a storage device such as a hard drive or an online server. Furthermore, in relation to detecting acoustic signals, the method 100 can additionally or alternatively include processing the set of acoustic signals according to at least one conditioning algorithm. For instance, for a given transmitter/detector pair of transducers, processing the set of acoustic signals can include one or more of: reading and correcting the raw data (detected acoustic signals) for DC variation; implementing a trapezoidal filter to bandpass useful frequencies and cut noise; and implementing any other suitable filter (high pass, low pass, etc.) to filter desired frequencies. Further signal processing can additionally or alternatively include discarding unusable signal such as "muting" in which recorded signal before the transmission wavefront and/or and after the longest applicable receiving time (e.g., "top muting" or "bottom muting"), further noise reduction processes, and other suitable signal processing steps. However, any other suitable conditioning process can additionally or alternatively be used.

1.2 Method—Reconstruction Problem Statement

Figure 3:
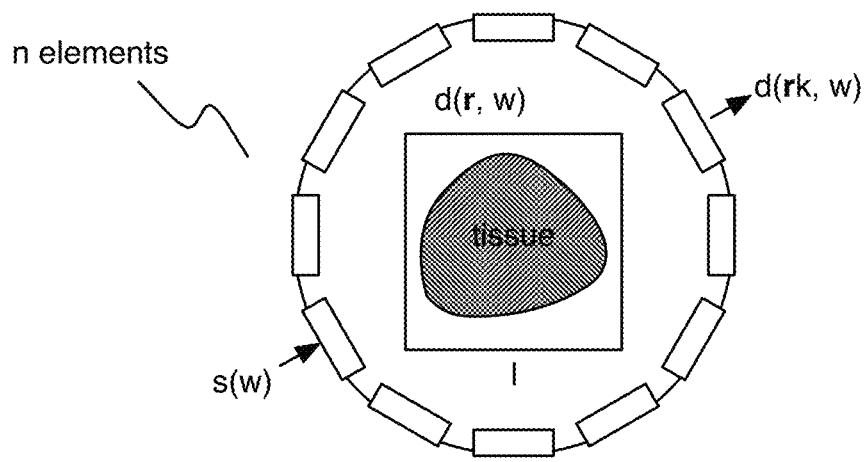
FIG. 3 depicts a schematic of a transducer ring and volume of tissue associated with a portion of an embodiment of an ultrasound waveform tomography method.

In one variation, as shown in FIG. 3, a volume of tissue (e.g., breast tissue) is immersed in acoustic coupling medium (e.g., water), and surrounded by a ring transducer 220 with n elements. In this variation, the considered region of interest (ROI) is a square of size l, whose origin is at the center of the ring transducer 220. The positions of the transducer elements, as shown in FIG. 3, are given by $r_k$, for k=1, 2, . . . , n.

In this variation, one goal is to estimate a real-valued acoustomechanical parameter model, which in a specific example is a sound speed model, c(r), within the ROI, as a means to quantitatively characterize the distribution of the acoustomechanical parameter across the ROI of the volume of tissue. While sound speed is modeled in the specific example, attenuation can be modeled with inclusion of an imaginary component to the sound speed model. In particular, in the specific example, the sound speed is assumed to be independent of frequency, such that there is no dispersion. However, in variations of the problem, the sound speed and/or any other relevant acoustomechanical parameter can be considered to have some dependence upon frequency. While reconstruction of the acoustomechanical parameter model of the volume of tissue is a three-dimensional problem, in this variation, reconstruction is performed on a series of two-dimensional slices (e.g., coronal slices of a volume of breast tissue), wherein the inter-slice spacing is adjusted as a function of a vertical span of the transducer beam emitted by the ring transducer 220, in order to ensure full coverage of the volume of breast tissue. In particular, although wave propagation is a 3D problem due to out of plane scattering, variations of the method 100 assume that the transducer ring 220 focuses most of the acoustic energy in a coronal plane, thereby motivating modeling of 2D wave propagation. This assumption can improve computational speed and reduce complexity of hardware implemented; however, other variations of the method can alternatively model 3D wave propagation. In this variation, the acoustomechanical parameter model is sampled on a uniform m×m reconstruction grid and organized into an $m^2$ dimensional vector c; however, the acoustomechanical parameter model can be sampled and/or organized in any other suitable manner.

In relation to acquisition, as described in Blocks S110 and S120 above, each transducer element of the transducer ring 220 can emit (e.g., sequentially emit) an ultrasound pulse, which propagates throughout the acoustic coupling medium. In the frequency domain, the pulse emitted by the transducer, with operating frequency ω, is given by the complex valued quantity s(ω), and the resulting wavefield at position r is denoted d(r, ω). As such, the experimental wavefield measured at transducer locations $r_k$ is given by d(r, ω), and the measurements obtained for all emitter-receiver pairs of the ring transducer 220 can be organized into an $n^2$ dimensional vector, $d_{obs}(\omega)$.

In this variation, the expected numerical wavefield obtained at position r for a given operating frequency ω and sound speed model c is denoted u(r, ω, c) and, similar to the experimental measurements, the simulated wavefield is sampled at the transducer locations and the values are organized in an $n^2$ dimensional vector u(ω, c).

Thus, the goal is to estimate the acoustomechanical parameter model (e.g., sound speed model), c, that generates, upon numerical simulation, simulated measurements $u_{obs}(\omega, c)$, that best matches the experimental measurements, $d_{obs}(\omega)$. In one example, this can be accomplished by minimizing the error cost function, E, noted in expression [1], where $^H$ denotes the Hermitian transpose, and wherein e is the residual mismatch defined in expression [2]:

$$E(\omega,c)=\frac{1}{2}e^H(\omega,c)e(\omega,c) \quad [1]$$

$$e(\omega,c)=u_{obs}(\omega,c)-d_{obs}(\omega,c) \quad [2]$$

In minimizing the error cost function, a regularization term can be added to smooth the reconstructed images based upon the acoustomechanical parameter model after iterative reconstruction, wherein the regularization term is configured to stabilize the matrix inversion process. As such, the process described is performed on one frequency ω at a time, with dependency between an iteration of the simulated wavefield and the corresponding iteration of the acoustomechanical parameter model. Furthermore, while one variation of minimizing an error cost function E is described above, in alternative variations of estimation of the acoustomechanical parameter model, any other suitable error reduction technique can be used.

Application of the above optimization problem is described in subsequent section of the method 100 below.

1.3 Method—Waveform Tomography Reconstruction

As shown in FIG. 1, an embodiment of the method 100 includes: generating, from the set of acoustic signals, an initial model representing a distribution of an acoustomechanical parameter across a region of the volume of tissue S130, extracting a subset of a frequency spectrum, including a set of frequency components, from the set of acoustic signals S140, generating a first simulated wavefield with a first frequency component of the set of frequency components S150, generating an updated model of the initial model with the first simulated wavefield S160; iteratively refining the updated model with a set of simulated wavefields associated with the set of frequency components until a threshold condition is satisfied, thereby producing a final model S170. Blocks S130-S170 function to implement a waveform tomography reconstruction algorithm that can be used to generate an enhanced rendering of the volume of tissue. Blocks S130-S170 are preferably implementing at a computing system, wherein the computing system can be implemented in one or more of a computer of a workstation associated with the transducer, a remote server, a cloud-based computing system, a computing module of a mobile computing device, and any other suitable computing module.

1.3.1 Waveform Tomography Reconstruction—Initial Model

Block S130 recites; generating, from the set of acoustic signals, an initial model representing a distribution of an acoustomechanical parameter across a region of the volume of tissue, which functions to provide a starting model of an acoustomechanical parameter that can be iteratively refined with simulated wavefields according to the waveform tomography reconstruction process described in subsequent blocks of the method 100. The initial model is preferably a model representing a distribution of sound speed across the region of the volume of tissue; however, the initial model can additionally or alternatively represent a distribution of any other suitable acoustomechanical parameter (e.g., attenuation, reflection) across at least a region of the volume of tissue.

In variations wherein the initial model is a sound speed model, the sound speed model is preferably based upon processing of through-transmission signals of the set of acoustic signals, which are received in Blocks S110 and S120 in addition to backscattered signals from the volume of tissue. Preferably, generation of the sound speed model includes generating a set of 2D slices representing sound speed, wherein each slices in the set of 2D slices represents a distribution of a sound speed parameter (e.g., a speed of sound at each of a set of regions within the volume of tissue) within the tissue, to form a stack of 2D slices representing sound speed across slices of the volume of tissue. In a specific example, the stack of 2D slices corresponds to regions of the volume of tissue generated in a posterior-anterior direction (e.g., from a chest wall to a nipple region of a volume of breast tissue); however, in other variations of the specific example, the stack of 2D slices can alternatively correspond to slices of the volume of tissue generated in any other direction (e.g., medial-lateral direction, inferior-superior direction, anterior-posterior direction, direction angled from an anterior-posterior direction, direction angled from a medial-lateral direction, direction angled from an inferior-superior direction, etc.). Each sound speed slice preferably includes multiple elements (e.g., pixels in a grid) such that each element has an associated value of the sound speed parameter for a respective region of the scan region, including the volume of tissue and the acoustic coupling medium (such as the fluid of the tank in which the tissue is submerged). Furthermore, each sound speed slice of the sound speed model is preferably a planar slice; however, the stack of slices for sound speed can be generated in any other suitable manner.

Generating a sound speed model in Block S130 can additionally or alternatively include generating a 3D sound speed model that is a volumetric representation of the sound speed parameter within the volume of tissue. In a first variation, as shown in FIG. 3, generating a 3D sound speed model can include combining a stack of 2D sound speed slices into a three-dimensional (3D) sound speed model. In a second variation, generating a 3D sound speed model can include transforming 3D volumetric acoustic data, obtained by scanning the tissue in a 3D manner, directly into a 3D sound speed map. Additionally or alternatively, the sound speed model can be generated using methods as described in U.S. Pat. No. 8,663,113 and/or U.S. Pub. No. 2012/0283566, filed on 23 Jul. 2012, which are each incorporated herein in its entirety by this reference.

In generating an initial sound speed model of the variation described above, Block S130 can comprise generating an initial sound speed model according to a travel time tomographic method, wherein the initial sound speed model has a sufficiently high degree of accuracy in order to avoid phase reconstruction mismatches resulting from $2\pi$ periodicity of the frequency components used in Block S140 and subsequent blocks of the method 100. Travel time tomographic methods implemented in this variation of Block S130 can be performed according to embodiments, variations, and examples described in one or more of: U.S. application Ser. No. 12/033,789 entitled "Automatic Time-of-Flight Selection for Ultrasound Tomography" and filed on 19 Feb. 2008; U.S. Pat. No. 8,870,771 entitled "Method and Apparatus for Categorizing Breast Density and Assessing Cancer Risk Utilizing Acoustic Parameters" and filed on 5 May 2008; U.S. Pat. No. 8,876,716 entitled "Method of Characterizing Breast Tissue using Multiple Ultrasound Renderings" and filed on 14 Feb. 2011; U.S. application Ser. No. 13/368,169 entitled "System and Method for Imaging a Volume of Tissue" and filed on 7 Feb. 2012; U.S. application Ser. No. 13/566,778 entitled "Method and System for Multi-Grid Tomographic Inversion Tissue Imaging" and filed on 3 Aug. 2012; U.S. application Ser. No. 13/756,864 entitled "Method and System for Denoising Acoustic Travel Times and Imaging a Volume of Tissue" and filed on 1 Feb. 2013; and U.S. application Ser. No. 14/703,746 entitled "Method for Representing Tissue Stiffness" and filed on 4 May 2015, which are each incorporated herein in its entirety by this reference. However, any other suitable non-travel time-based algorithm can be used in generating the initial model of Block S130.

In a specific example, the initial sound speed model is reconstructed using a travel time tomographic algorithm on a square ROI of size l=228 mm, whose origin is at the center of the transducer ring (with the same ROI used for all reconstructions). In the specific example, the initial sound speed model is iteratively refined according to the travel time tomographic algorithm in a manner that reduces the effects of strong ray artifacts that could adversely affect a final model generated using the initial model. As such, generation of the initial sound speed model can be performed with iteration according to the travel time tomography algorithm, until ray artifact reduction satisfies an artifact threshold condition (e.g., number of artifacts, resolution of artifacts, etc.). However, variations of the specific example can use any other suitable ROI that enables an enhanced image of a ROI of the volume of tissue to be generated, any other suitable iterative or non-iterative process, and/or any other suitable condition that removes artifacts that could corrupt a final reconstruction. Furthermore, similar processes to those described above can be adapted to generation of an initial model based upon any other suitable acousto-mechanical parameter, in Block S130.

1.3.2 Waveform Tomography Reconstruction—Frequency Component Extraction

Block S140 recites: extracting a subset of a frequency spectrum, including a set of frequency components, from the set of acoustic signals, which functions to generate inputs for the iterative reconstruction algorithm performed in Blocks S150-S170 of the method 100, which in some variations, can model a Helmholtz equation through a finite difference approach. In extracting the subset of the frequency spectrum, Block S140 preferably comprises extracting the subset of the frequency spectrum from raw ultrasound signal data associated with the set of acoustic signals of Block S120; however, Block S140 can additionally or alternatively comprise extracting the subset of the frequency spectrum from data derived from the transducer of Block S110 in any other suitable manner.

In some variations, Block S140 can comprise preprocessing raw ultrasound data received in Block S120 prior to extraction of the subset of the frequency spectrum, wherein preprocessing can comprise one or more of: time windowing data derived from the set of acoustic signals S141; damping data derived from the set of acoustic signals S142; selecting waveforms of data derived from the set of acoustic signals S143; performing a Fourier transformation on data derived from the set of acoustic signals S144; accounting for a beam profile of the transducer S145 in preprocessing the raw ultrasound data; and performing an estimation of a signal source scaling factor S146.

Block S141 recites: time windowing data derived from the set of acoustic signals, which functions to enable extraction of a primary transmitted portion of a waveform received at the receiver(s) of the transducer, and to reject reflected and/or multi-scattered signals. As such, the iterative reconstruction algorithm can be focused on information contained in the primary transmitted portion of the signal, without interference of non-primary signal portions. In one variation, Block S141 comprises estimating the time of first arrival for each waveform of the set of acoustic signals received in Block S110, based upon an automatic travel time selection algorithm, embodiments, variations, and examples of which are described in U.S. application Ser. No. 12/033,789 entitled "Automatic Time-of-Flight Selection for Ultrasound Tomography" and filed on 19 Feb. 2008. In addition to the time of first arrival for a waveform, this variation of Block S141 comprises selecting a span of the time window to include contribution of the primary transmitted waveform. Furthermore, this variation of Block S141 comprises applying sinusoidal tapers (e.g., cosine tapers of 0.5 µs) to the boundaries of the time windowed data in order to avoid aliasing in the frequency domain. However, variations of Block S141 can additionally or alternatively implement any other suitable time windowing technique for isolating the primary transmitted portion of a waveform from reflected and/or multi-scattered signals, with or without any other suitable taper applied to boundaries of the time-windowed data.

Block S142 recites: damping data derived from the set of acoustic signals, which functions to focus the iterative reconstruction algorithm implemented in subsequent blocks of the method 100 on information contained in the primary transmitted portion of the signal, without interference of non-primary signal portions. In one variation, Block S142 includes applying an exponential damper to each waveform of the set of acoustic signals received in Block S110, wherein the exponential damper is applied to the tail of each associated signal. In more detail, the exponential damper can have a profile of the form: $\max\{1, \exp(-(t-t_o-t_d)/\dagger\}$, wherein in a specific example, $t_d$ is selected to correspond to the time length of the first reverberation of the received signal (e.g., 5 µs) after the travel time $t_o$, and a scaling factor $\dagger$ (e.g., 1 µs) is used to attenuate a later portion of the signal that is contaminated by non-transmitted components. However, variations of Block S142 can additionally or alternatively comprise any other suitable damper function (e.g., non-exponential damper function), applied to any other suitable portion of an acoustic waveform.

Figure 4:
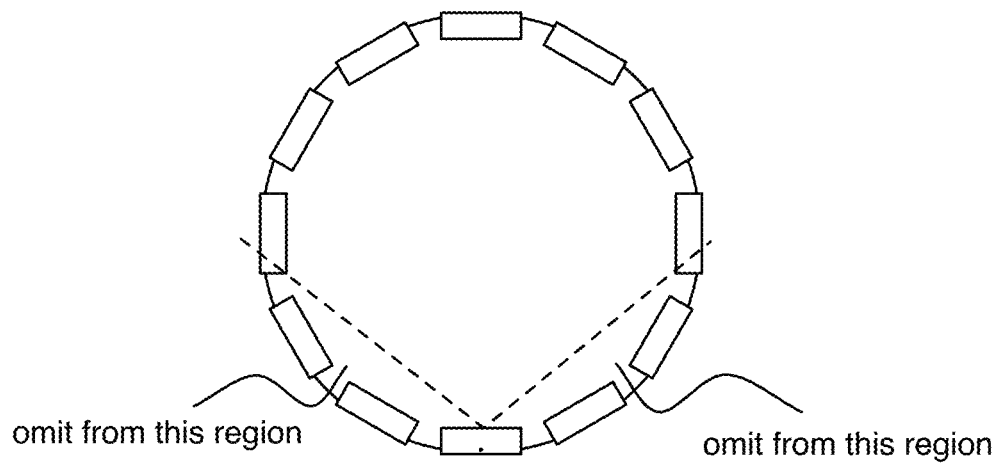
FIG. 4 depicts a variation of a portion of signal preprocessing in an embodiment of an ultrasound waveform tomography method.

Block S143 recites: selecting waveforms of data derived from the set of acoustic signals, which functions to omit consideration of waveforms of the set of acoustic signals that are associated with faulty transducer elements and/or include above a threshold level of noise that reduces efficiency of the iterative reconstruction process described in subsequent blocks of the method 100. In one variation, Block S143 comprises receiving calibration information associated with calibration of the transducer (e.g., according to embodiments, variations, and examples of the methods described in U.S. Pat. No. 8,532,951 entitled "Method for Calibrating a Transducer Array" and filed on 22 Dec. 2010, which is herein incorporated in its entirety by this reference), wherein the calibration information is used to discard waveforms associated with faulty transducer elements. In more detail, waveforms associated with a faulty receiving element and/or a faulty transmitting element can be discarded in Block S143. Block S143 can additionally or alternatively include discarding waveforms associated with small angle emitter-receiver pairs. For instance, in one example, directional beam profiles of the transducer elements can cause small angle emitter-receiver contributions to be unreliable, and Block S143 can comprise omitting waveforms that lie outside of an arc of 270° with respect to the associated emitter of the transducer, as shown in FIG. 4. However, Block S143 can additionally or alternatively include selection and/or discarding of waveforms in association with any other suitable transducer configuration, any other suitable transducer beam profile(s) of transducer elements, any other suitable noise-contributing factor, and any other suitable factor.

Figure 5:
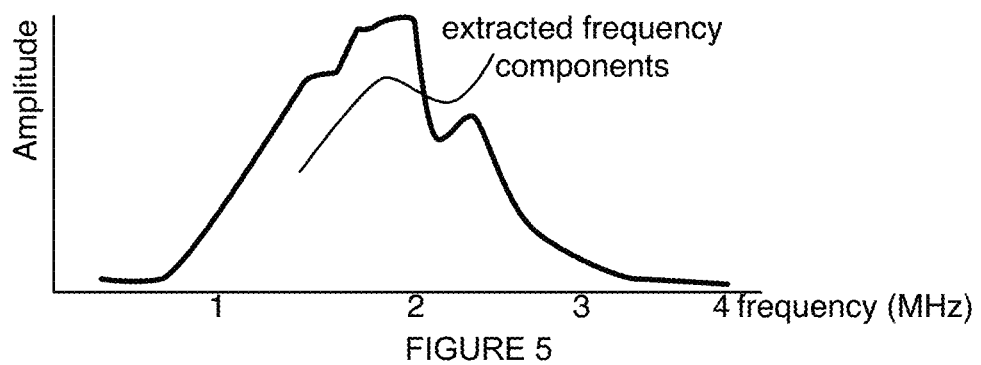
FIG. 5 depicts an example of extracted frequency components in an embodiment of an ultrasound waveform tomography method.

Block S144 recites: performing a Fourier transformation on data derived from the set of acoustic signals, which functions to extract the set of frequency components, of the frequency spectrum, which are used as frequency inputs in the iterative reconstruction process implemented in subsequent blocks of the method 100. In more detail, the set of frequency components extracted in Block S144 and used in subsequent blocks of the method 100 preferably satisfy an energy threshold, and in a specific example, comprises frequency components between 400 kHz and 1 MHz, distributed in increments of 30 kHz. However the set of frequency components extracted in Block S144 can additionally or alternatively comprise any other suitable range of frequencies, with any other suitable distribution (e.g., in relation to a central frequency of the frequency spectrum), wherein an example frequency spectrum is shown in FIG. 5. In relation to the iterative reconstruction process described in more detail below, in one variation, iteration can be performed multiple times on each frequency, followed by iteration at a subsequent frequency until each of the set of frequency components is used. This variation is configured to gradually incorporate shorter wavelength features, in order to prevent the reconstruction algorithm from stalling or otherwise terminating prematurely (e.g., due to a local minima effect, etc.). However, as described in more detail below, the iterative reconstruction can process frequency components extracted from the frequency spectrum in any suitable order, with any suitable number of iterations at each frequency component.

Block S145 recites: accounting for a beam profile of the transducer S145 in preprocessing the raw ultrasound data, which functions to further enhance alignment between simulated results and experimental results in association with iterations of the acoustomechanical parameter model. Block S145 can comprise including a response of the transducer in a propagation model implemented in the iterative reconstruction algorithm, described in further detail below. Block S145 can additionally or alternatively include modifying the waveforms of the set of acoustic signals received in Block S120 to match a numerical model (e.g., a numerical model that assumes ultrasound emission from omni-directional point sources). In a specific example of modifying the waveforms to match a numerical model that assumes emission from omni-directional point sources, Block S145 can include normalizing the magnitude spectrum of both the simulated and the experimental datasets, in order to match the phases of the frequency components during the inversion process of the iterative reconstruction process. In relation to the specific example, Block S145 can further include matching the amplitudes of the frequency components (i.e., to prevent effects of residual artifacts resulting from propagation medium rich with scattering) during the inversion process of the iterative reconstruction process described below; however, accounting for the beam profile of the transducer in Block S145 can additionally or alternatively be implemented in any other suitable manner.

Block S146 recites: performing an estimation of a signal source scaling factor, which functions to facilitate determination of solutions to the forward modeling process described in relation to Block S150 below. In a specific example, for a given sound speed model, estimation of the signal source scaling factor is a linear estimation problem, wherein determination of a complex valued signal source scaling factor γ provides alignment between simulated and experimental results in a mean squared sense. In the specific example, Block S146 comprises determination of γ according to expression [3]:

$$\gamma = [d^H_{obs} u_{obs}] / [u^H_{obs} u_{obs}] \qquad [3]$$

wherein, given a ring transducer in the specific example, a single scaling factor can be computed by matching the data gathered from all emitters of the ring transducer. In relation to subsequent blocks of the method 100, the iterative reconstruction algorithm can alternative between estimation of a sound speed model for a given source signal within one iteration, and updating the source signal using the scaling factor γ determined according to expression [3] for a known sound speed model.

Preprocessing the raw ultrasound data to extract the frequency components in Block S140 can, however, include any other suitable steps or blocks.

1.3.3 Waveform Tomography Reconstruction—Forward Modeling

Figure 6:
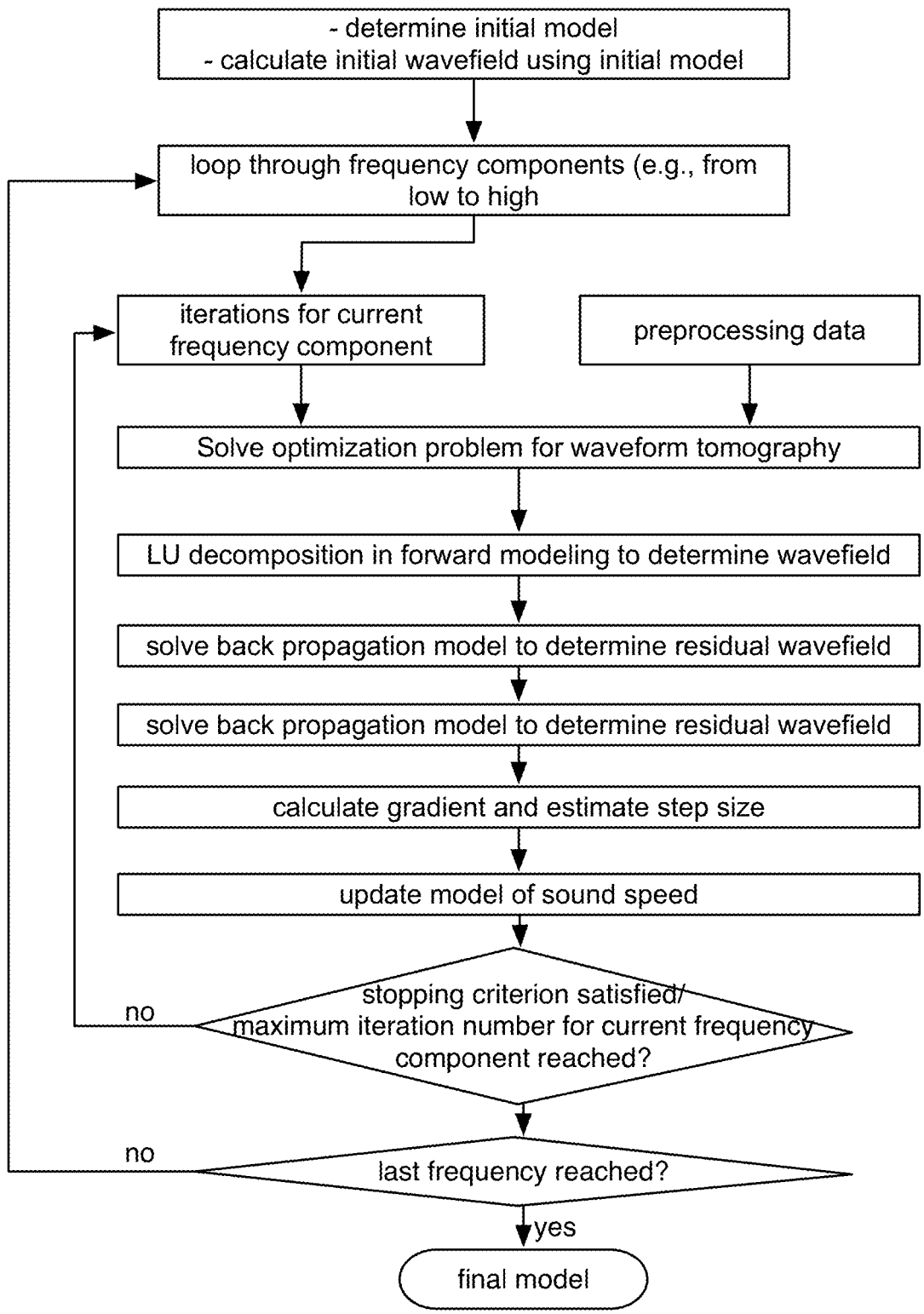
FIG. 6 depicts an example schematic flowchart of an ultrasound waveform tomography method.

Block S150 recites: generating a first simulated wavefield with a first frequency component of the set of frequency components, which functions to initiate a first portion of an iterative algorithm that refines the acoustomechanical parameter model used to generate the enhanced image of Block S180. In particular, the iterative reconstruction algorithm initiates with the initial model of Block S130, which is iteratively updated according to a gradient descent method. The iterations stop when a convergence criterion is satisfied, as shown in FIG. 1, and in the example of FIG. 6. In more detail, computation of a simulated wavefield at a given iteration is performed through a forward modeling process, as described further in Block S150, and iterative refinement of the initial model is performed based upon a computed measurement mismatch obtained upon generating a solution to an inverse problem. However, iterative refinement can additionally or alternatively be performed according to any other suitable process.

In one variation, a forward modeling process implemented in Block S150 includes modeling propagation of acoustic waves in the frequency domain through a finite difference approach, wherein in a specific example, modeling of acoustic waves implements a Helmholtz equation provided below as expression [4], where $\nabla^2$ is the Laplacian operator, $[\nabla^2 + \omega^2/c(r)^2]$ is the Helmholtz operator S, ω is the frequency component associated with the current iteration, c is the sound speed model, u is the expected numerical wavefield obtained at transducer position r for frequency ω, and s represents the spatial source.

$$[\nabla^2 + \omega^2/c(r)^2] u(r, \omega) = s(r, \omega) \qquad [4]$$

In expression [4], in the case where s is a point source at position $r_k$, as shown in FIG. 3, s(r, ω) can be expressed as s(ω) δ(r−$r_k$), where δ denotes the delta distribution. In one variation of numerically solving expression [4] at a computing system, the computing system is configured to sample the wavefield values on a uniform m×m simulation grid (i.e., the dimensions of the simulation grid(s) and the reconstruction grid(s) do not need to match). The characteristic grid dimension (i.e., size of each grid element) can be computed as $\lambda/n_\lambda$, where λ is the wavelength at the frequency component (e.g., a selected optimization frequency) of the current iteration, and n, is a number of grid points per wavelength that satisfies a threshold condition for avoiding numerical dispersion at the frequency of the current iteration. In relation to determination of the wavelength λ, implementation of the variation described above involves use of the mean acoustomechanical parameter value (e.g., sound speed value) of the acoustic coupling medium (e.g., of the water bath surrounding the volume of tissue) as a reference value.

Similar to processes described above, the wavefield values can be organized into an $m^2$ dimensional vector u, and an $m^2$ dimensional vector s can be constructed that has non-zero values only at the grid indices corresponding to the position of the transmitting transducer element; however, the wavefield values of u and the vector s can alternatively be organized in any other suitable manner in implementing Block S150. In this variation, a single index of s can be illuminated to simulate a point source (as in the specific system configuration described above); however, a combination of indices of s having values of different magnitudes and/or phases can be illuminated in relation to other system configurations with different transducer responses than that of the specific system configuration described above. Similarly, the Helmholtz operator shown in expression [4] is discretized using a finite difference approach, and values of the Helmholtz operator are organized in a matrix S with dimensions $m^2 \times m^2$, wherein S is large but sparse. Furthermore, the entries of S depend upon the assumed acoustomechanical parameter model (e.g., sound speed model) and boundary conditions (e.g., absorbing boundary conditions, etc.). In a specific example, the finite difference approach uses nine-point finite difference stencils, and absorbing boundary conditions for first and/or second order wave equations, with the matrix form of the Helmholtz equation of expression [4] provided as expression [5]:

$$Su=s \qquad [5]$$

Expression [5] can be solved for each source signal of the set of acoustic signals received in Block S120, but can alternatively be solved for a subset of source signals of the set of acoustic signals. Furthermore, since S does not change unless the sound speed model is updated, the systems of equations of expressions [1] through [5] can be solved using LU factorization. In more detail, once S has been factored, its LU constituents can be re-used to rapidly solve the system of equations corresponding to each source signal of the transducer ring. Furthermore, alternative variations of the above process can use any other suitable factorization process (e.g., Rank factorization, Cholesky decomposition, QR decomposition, RRQR factorization, interpolative decomposition, etc.).

In implementation of the forward modeling process, Block S150 can include assuming that propagation of acoustic waves within the volume of tissue is governed by an acoustic wave equation with constant density; however, Block S150 can alternatively omit use of an acoustic wave equation with a constant density assumption.

1.3.4 Waveform Tomography Reconstruction—Inverse Problem and Iteration

Block S160 recites: generating an updated model of the initial model with the first simulated wavefield, which functions to initiate a second portion of an iterative algorithm that refines the acoustomechanical parameter model used to generate the enhanced image of Block S180. In Block S160, the updated model is preferably generated based upon multiple iterations using the first frequency component of the set of frequency components; however, the updated model can alternatively be generated based upon a single iteration using the first frequency component of the set of frequency components used to generate the first simulated wavefield of Block S150. In more detail, for a specific example of updating a sound speed model, the gradient of the cost function shown in expression [1] can be determined, and the sound speed model is updated according to expression [6], where $c^1$ is the current estimate of the sound speed model, $c^2$ is the next estimate of the sound speed model, $\alpha$ is a step size factor determined by a line search method (or alternatively, through liner approximation), and $\nabla E$ is the gradient of the cost function taken with respect to the real-valued sound speed:

$$c^2=c^1-\alpha\nabla E(\omega,c^1) \qquad [6]$$

In relation to variations of the method 100 applied to other acoustomechanical parameters (e.g., attenuation), updating a model according to the above variation of Block S160 can be performed on real and imaginary portions of a model independently.

In the example of updating the sound speed model above, the gradient of the cost function can be evaluated according to expression [7] as follows:

$$\nabla E = Re\{J^H e\} \qquad [7]$$

In expression [7], J is an $n^2 \times m^2$ Fréchet derivative matrix whose elements are given by expression [8], where $u_{obs,i}$ and $c_j$ are the i-th and j-th elements of the vectors $n_{obs}$ and c, respectively:

$$J_{i,j} = \delta u_{obs,i}/\delta c_j, \text{ for } i,j=1,2,3,\ldots,n^2 \qquad [8]$$

The derivatives of expression [8] can be approximated by taking the derivative of expression [5] with respect to the sound speed at each grid point, in order to obtain an expression for the gradient of the cost function, yielding expression [9], where the inverse operator $(*)^{-1}$ is shorthand for the LU decomposition and inversion process, and $f_j=-[\delta S/\delta c_j]u$ represents a virtual source:

$$\delta u/\delta c_j = -S^{-1}[\delta S/\delta c_j]u = S^{-1}f_j \qquad [9]$$

In order to determine $[\delta S/\delta c_j]$ in expression [9], Block S160 can include using the derivatives of finite difference equations, where expression [8] involves the wavefield values $u_{obs}$ at the transducer grid points, and expression [9] involves the wavefield values u at all grid points. As such, expression [8] can be augmented to generate an augmented Fréchet derivative matrix $\hat{J}$ of dimensions $m^2 \times m^2$ having coefficients provided as expression [10], where $u_i$ is the i-th element of the vector u:

$$\hat{J}_{i,j} = \delta u_i/\delta c_j, \text{ for } i,j=1,2,3,\ldots,m^2 \qquad [10]$$

Similarly, the residual vector e is augmented with zeroes to create an $m^2$ dimensional vector $\hat{e}$. Thus, considering each of the column vectors $f_j$ as a column of a matrix F, the augmented Fréchet matrix of expression [10] can be written according to expression [11]:

$$\hat{J} = S^{-1}[f_1 \ldots f_{m^2}] = S^{-1}F \qquad [11]$$

Thus, expression [7] simplifies to the expression shown as expression [12], where $v=[S^{-1}]^H\hat{e}$ is the back-propagated wavefield with the residual acting as a source:

$$\nabla E = Re\{\hat{J}^H \hat{e}\} = Re\{F^H[S^{-1}]^H \hat{e}\} = Re\{F^H v\} \qquad [12]$$

Block S170 recites: iteratively refining the updated model with a set of simulated wavefields associated with the set of frequency components until a threshold condition is satisfied, thereby producing a final model. Block S170 thus functions to achieve a final model of the acoustomechanical parameter model, which can be used to generate a high-resolution rendering of the volume of tissue in Block S180. Block S170 preferably includes iteration of Blocks S150 and S160 until a threshold condition is achieved, thereby generating a final model from which a high resolution image of the volume of tissue can be derived. As such, the expressions of the method 100 described above can be iteratively performed, with expression [6] modified as expression [13]:

$$c^{(i+1)} = c^i - \alpha\nabla E(\omega,c^i) \qquad [13]$$

In relation to the iterative reconstruction process described in Block S170, iteration can be performed multiple times on each frequency component of the set of extracted frequency components of Block S140, followed by iteration at a subsequent frequency until each of the set of frequency components is used. This process is configured to gradually incorporate shorter wavelength features, in order to prevent the reconstruction algorithm from stalling or otherwise terminating prematurely (e.g., due to a local minima effect, etc.). However, the iterative reconstruction can process frequency components extracted from the frequency spectrum in any suitable order, with any suitable number of iterations at each frequency component.

Iteration in Block S170 can, however, be performed in any other suitable manner.

1.4 Method—Outputs

Block S180 recites: generating the enhanced image from the final model of the volume of tissue, which function to provide an image of the volume of tissue that can be used for diagnostic and/or tissue mass characterization purposes. In variations wherein the volume of tissue is a volume of breast tissue, the enhanced image can be used to enable differentiation between benign and malignant masses including tumors (e.g., high sound speed tumors), parenchymas, and cysts, thereby assisting an operator of the system in detecting one or more pathologies within the volume of tissue.

In Block S180, the enhanced image is preferably rendered at a display of a user interface, wherein the display is in communication with the computing system (e.g., computer processor), such that the enhanced image can be provided to a user or an entity associated with the user having the volume of tissue analyzed. The enhanced image can, however, be rendered in any other suitable manner. In variations, one or more regions of interest of the volume of tissue can be highlighted in the enhanced image with one or more visual cues (e.g., color, pattern, shading) associated with different tissue mass types. However, rendering the enhanced image can additionally or alternatively be implemented in any other suitable manner, at any other suitable display.

In some variations, generating the enhanced image in Block S180 can further include providing an indication of at least one tissue mass within the volume of tissue at a user interface. Providing the indication can be used to indicate presence of a cancerous mass, or risk of developing a cancerous mass within the volume of tissue, as assessed by way of the enhanced image. Providing the indication can comprise generating an analysis at a module of the computing system, wherein generating the analysis includes generating the indication of presence of at least one target mass within the volume of tissue. In some embodiments, the indication can characterize a distribution of different tissue types within the volume of tissue, as such, the enhanced image (e.g., a 3D map or image, a 2D map or image, etc.) can be annotated with an indication of a distribution of one or more of: fat tissue (e.g., fatty parenchyma, parenchymal fat, subcutaneous fat, etc.), parenchymal tissue, cancerous tissue, abnormal tissue (e.g., fibrocystic tissue, fibroadenomas, etc.), cyst tissue, and any other suitable tissue type within the volume of tissue. The indication can be provided visually, for instance, using outlines or arrows to direct a viewer toward regions of the volume of tissue having the tissue mass(es) of interest. The indication can additionally or alternatively be provided in a text and/or audio format, by describing the location(s) of the tissue mass(es) within the volume of tissue, using anatomical terms of location. The indication is preferably provided to an entity analyzing the volume of tissue, wherein the entity can comprise a human entity or a computing entity (e.g., processing system, remote server, computer processor, cloud computing system, etc.). In variations, the human entity can include one or more of: a healthcare provider, a radiologist, a technician, a physician, a nurse, a caretaker, a system operator, a relative, an acquaintance, and any other suitable entity associated with the patient and/or interested in analysis of the volume of tissue.

In a specific example of an output of Block S180, the enhanced image can provide higher resolution in relation to features of interest of the volume of tissue, as shown in FIGS. 7A-7C. In more detail, FIG. 7A shows a reconstruction of a breast phantom using a traditional travel time tomography method, FIG. 7B shows a reconstruction of the breast phantom using an example of the method 100 described above, and FIG. 7C shows a computed tomography comparison image of the breast phantom, wherein resolution of features annotated as the numbers 1-6 in the waveform tomography reconstructed image approach those of the computed tomography image, without use of ionizing radiation.

In another specific example of an output of Block S180, enhanced images of in vivo structures of a patient's breast tissue more clearly show features of interest, as shown in FIGS. 8A-8C, in comparison to images generated according to a traditional travel time tomography algorithm, as shown in FIGS. 8D-8F. Furthermore, in this specific example, ray artifacts in the enhanced image are significantly reduced in comparison to the images generated according to the traditional travel time tomography algorithm.

The method 100 can, however, include any other suitable blocks or steps that facilitate detection, processing, and/or analyzing of acoustic signals generated from a volume of tissue of the user in a manner that provides an enhanced image of structures within the volume of tissue. Furthermore, as a person skilled in the art will recognize from the previous detailed description and from the figures and claims, modifications and changes can be made to the preferred embodiments of the method 100 without departing from the scope of method 100.

2. System

As shown in FIGS. 2A-2C, a system 200 for determining a distribution of a stiffness parameter within a volume of tissue comprises: a transducer 220 configured to receive the volume of tissue and comprising an array of ultrasound transmitters 110 and an array of ultrasound receivers 120, the array of ultrasound transmitters no configured to emit acoustic waveforms toward the volume of tissue and the array of ultrasound receivers 120 configured to detect a set of acoustic signals derived from acoustic waveforms transmitted through the volume of tissue; a computing system 210 in communication with the transducer, the computing system 210 comprising: a first module 212 configured to generate, from the set of acoustic signals, an initial model representing a distribution of an acoustomechanical parameter across a region of the volume of tissue; a second module 214 configured to extract a subset of a frequency spectrum, including a set of frequency components, from the set of acoustic signals; a third module 216 configured to generate a first simulated wavefield with a first frequency component of the set of frequency components; a fourth module configured to generate an updated model of the initial model with the first simulated wavefield, wherein the third and fourth modules 216, 218 are configured to iteratively refine the updated model with a set of simulated wavefields associated with the set of frequency components until a threshold condition is satisfied, thereby producing a final model; and a fifth module 219 configured to generate the enhanced image from the final model of the volume of tissue; and a display 290 in communication with the computing system 210 and configured to render the enhanced image of the volume of tissue.

The system 200 functions to render ultrasound images and/or generate transformed ultrasound data that can be used to generate a high resolution image of structures present within a volume of tissue. In some embodiments, the system 200 can function to produce images that are aligned with regulatory standards for medical imaging, as regulated, for instance, by the U.S. Food and Drug Administration (FDA).

The system 200 is preferably configured to implement at least a portion of an embodiment, variation, or example of the method 100 described in Section 1 above; however, the system 200 can additionally or alternatively be configured to implement any other suitable method.

The transducer 220, the computer processor 210, and the display 290 are preferably coupled to a scanner table 205, as shown in FIGS. 2A and 2B, wherein the scanner table 205 has an opening 206 that provides access to the volume of tissue 10 of the patient. The table, which may be made of a durable, flexible material (e.g., flexible membrane, fabric, etc.), preferably contours to the patient's body, thereby increasing scanning access to the axilla regions of the breast and increasing patient comfort. The opening 206 in the table allows the breast (or other appendage) to protrude through the table and be submerged in an imaging tank 230 filled with water or another suitable fluid as an acoustic coupling medium that propagates acoustic waves.

As shown in FIGS. 2B and 2C, a ring-shaped transducer 220 with transducer elements 222 can be located within the imaging tank 230 and encircle or otherwise surround the breast, wherein each of the transducer elements 222 can comprise one of the array of ultrasound transmitters 110 paired with one of the array of ultrasound receivers 120. Multiple ultrasound transmitters 110 that direct safe, non-ionizing ultrasound pulses toward the tissue, and multiple ultrasound receivers 120 that receive and record acoustic signals scattering from the tissue and/or transmitted through the tissue, are distributed around the ring transducer 220. In one configuration, the transducer 220 can be organized such that each ultrasound transmitter element is paired with a corresponding ultrasound receiver element, each ultrasound transmitter element is surrounded by two adjacent ultrasound transmitter elements, each ultrasound receiver element is surrounded by two adjacent ultrasound receiver elements, and the transducer is axially symmetric, as in FIG. 2C. During the scan, the ring transducer 220 passes along the tissue, such as in an anterior-posterior direction between the chest wall and the nipple region of the breast to acquire an acoustic data set including measurements such as acoustic reflection, acoustic attenuation, and sound speed, preferably at discrete scanning steps, or coronal "slices". The transducer 220 can be configured to scan step-wise in increments from the chest wall towards the nipple, and/or from the nipple towards the chest wall. However, the transducer 220 may additionally and/or alternatively receive data regarding any suitable biomechanical property of the tissue during the scan, and in any suitable direction.

In some embodiments, the scanner table can comprise an embodiment, variation, or example of the patient interface system described in U.S. application Ser. No. 14/208,181 entitled "Patient Interface System" and filed on 13 Mar. 2014, which is hereby incorporated in its entirety by this reference. Furthermore, in a specific example, the system 200 can implement a ring transducer 220 having 2048 transducer elements in cooperation with an ultrasound tomographic scanner 200 having 512 receive channels, 512 transmit channels, an operating frequency of 3 MHz, a data resolution of 14 bits, an image resolution of 0.7 mm, a slice thickness of 2.5 mm, a reconstruction time per slice of 15 seconds, and an ability to accommodate volumes of tissue 22 cm in diameter. However, system 200 can additionally or alternatively comprise or be coupled with any other suitable patient interface system.

The computing system 210 can be implemented in one or more computing systems, wherein the computing system(s) can be implemented at least in part in the cloud and/or as a machine (e.g., computing machine, server, etc.) configured to receive a computer-readable medium storing computer-readable instructions. Additionally or alternatively, the computer processor can be implemented on one or more computer networks, computer systems, or applications servers, etc., wherein the computer system(s) can comprise one or more of: a cloud-based computer, a mainframe computer system, a grid-computer system, or any other suitable computer system. In one variation, the first module 212, the second module 214, the third module 216, the fourth module 218, and the fifth module 219 of the computing system 210 are implemented as software modules executing on a computer machine coupled to the scanner table 205 and in communication with the display 290; however, the computing system 210 can additionally or alternatively be implemented using any other suitable computing system architecture.

The system 200 can include any other suitable elements that facilitate detection, processing, and/or analyzing of acoustic signals generated from a volume of tissue of the user in a manner that provides a representation of stiffness within the volume of tissue. Furthermore, as a person skilled in the art will recognize from the previous detailed description and from the figures and claims, modifications and changes can be made to the preferred embodiments of the system 200 without departing from the scope of system 200.

The FIGURES illustrate the architecture, functionality and operation of possible implementations of systems, methods and computer program products according to preferred embodiments, example configurations, and variations thereof. In this regard, each block in the flowchart or block diagrams may represent a module, segment, step, or portion of code, which comprises one or more executable instructions for implementing the specified logical function(s). It should also be noted that, in some alternative implementations, the functions noted in the block can occur out of the order noted in the FIGURES. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The method 100 of the preferred embodiment can be embodied and/or implemented at least in part as machine configured to receive a computer-readable medium storing computer-readable instructions. The instructions are preferably executed by computer-executable components preferably integrated with the system and one or more portions of the processor and/or analysis engine. The computer-readable medium can be implemented in the cloud, and/or stored on any suitable computer-readable media such as RAMs, ROMs, flash memory, EEPROMs, optical devices (CD or DVD), hard drives, solid state drives, or any suitable device. The computer-executable component is preferably a general or application specific processor, but any suitable dedicated hardware or hardware/firmware combination device can alternatively or additionally execute the instructions.

As a person skilled in the art will recognize from the previous detailed description and from the figures and claims, modifications and changes can be made to the preferred embodiments of the invention without departing from the scope of this invention defined in the following claims.

We claim:

1. A method for generating an enhanced image of a volume of tissue, the method comprising:
   with a transducer comprising an array of ultrasound transmitters and an array of ultrasound receivers and configured to surround the volume of tissue, emitting acoustic waveforms toward the volume of tissue with the array of ultrasound transmitters, wherein the acoustic waveforms comprise a frequency spectrum comprising a plurality of frequency components within the frequency spectrum sufficient to resolve a lesion within the volume of tissue;
   detecting, with the array of ultrasound receivers, a set of acoustic signals derived from acoustic waveforms transmitted through the volume of tissue;
   at a computing system in communication with the transducer, generating, from the set of acoustic signals, an initial sound speed model representing a distribution of sound speed across a region of the volume of tissue;
   at the computing system, extracting a subset of the frequency spectrum, including a set of the frequency components within the frequency spectrum, from the set of acoustic signals;
   at the computing system, generating a first simulated wavefield of a set of simulated wavefields with a first frequency component of the set of frequency components within the frequency spectrum, according to a forward modeling process;
   at the computing system, generating an updated model representing an updated distribution of sound speed across the region of the volume of tissue based upon a solution to an inverse problem generated with the first simulated wavefield;
   iteratively refining the updated model at a plurality of subsequent frequencies within the set of frequency components with solutions to the inverse problem, wherein the solutions are generated with the set of simulated wavefields associated with the set of frequency components within the frequency spectrum until a threshold condition is satisfied, thereby producing a final sound speed model; and
   at a display in communication with the computing system, rendering a sound speed image, generated from the final sound speed model of the volume of tissue.

2. The method of claim 1, wherein generating the initial sound speed model comprises generating the initial sound speed model according to a travel time tomography algorithm with iteration until reduction of ray artifacts in the initial sound speed model satisfies an artifact threshold condition.

3. The method of claim 1, wherein extracting the set of frequency components from the set of acoustic signals includes: time windowing data derived from the set of acoustic waveforms, according to a travel time selection algorithm that identifies primary transmitted portions of the set of acoustic signals; and applying sinusoidal tapers to boundaries of time windowed data derived from the set of acoustic waveforms.

4. The method of claim 1, wherein extracting the set of frequency components from the set of acoustic signals includes: discarding waveforms of the set of acoustic signals associated with emitter-receiver pairs of the transducer outside of an arc of 270 degrees.

5. The method of claim 1, wherein generating the first simulated wavefield of the set of simulated wavefields with the first frequency component modeling propagation of acoustic waves transmitted through the volume of tissue according to a Helmholtz operation expressed as:

$$[\nabla^2+\omega^2/c(r)^2]u(r,\omega)=s(r,\omega), \text{ where}$$

$\nabla^2$ is the Laplacian operator, and
$[\nabla^2+\omega^2/c(r)^2]$ is a Helmholtz operator, including $\omega$ as the first frequency component, c as the initial sound speed model, u as an expected numerical wavefield obtained at positions r of the transducer for the first frequency component $\omega$, and
s is a spatial ultrasound source of the transducer.

6. The method of claim 1, wherein iteratively refining the updated model with solutions to the inverse problem comprises performing multiple iterations at each of the set of frequency components in sequence, until a final frequency component of the set of frequency components is processed.

7. The method of claim 1, wherein the set of acoustic signals are derived from acoustic waveforms transmitted through a plurality of two-dimensional imaging panes through the volume of tissue.

8. The method of claim 1, wherein generating the updated model of the initial sound speed model comprises performing an iterative process that processes the initial model with a gradient of an error cost function, wherein the gradient of the error cost function includes a component derived from the first simulated wavefield.

9. The method of claim 8, wherein the iterative process is expressed as:

$$c^2=c^1-\alpha\nabla E(\omega,c^1), \text{ where}$$

$c^2$ is the updated model of the initial sound speed model,
$c^1$ is the initial sound speed model,
$\alpha$ is a step size,
$\nabla E$ is the gradient of the error cost function, and
$\omega$ is the first frequency component of the set of frequency components.

10. A method for generating an enhanced image of a volume of tissue, the method comprising:
   with a transducer comprising an array of ultrasound transmitters and an array of ultrasound receivers and configured to surround the volume of tissue, emitting acoustic waveforms toward the volume of tissue with the array of ultrasound transmitters, wherein the acoustic waveforms comprise a frequency spectrum comprising a plurality of frequency components within the frequency spectrum sufficient to resolve a lesion within the volume of tissue;
   detecting, with the array of ultrasound receivers, a set of acoustic signals derived from acoustic waveforms interacting with the volume of tissue;
   at a computing system in communication with the transducer, generating, from the set of acoustic signals, an initial model representing a distribution of an acousto-mechanical parameter across a region of the volume of tissue;
   at the computing system, extracting a subset of the frequency spectrum, including a set of the frequency components within the frequency spectrum, from the set of acoustic signals;
   at the computing system, generating a first simulated wavefield of a set of simulated wavefields with a first frequency component of the set of the frequency components within the frequency spectrum;

at the computing system, generating an updated model of the initial model with the first simulated wavefield representing an updated distribution of sound speed across the region of the volume of tissue iteratively refining the updated model at a plurality of subsequent frequency components within the set of the frequency components with the set of simulated wavefields associated with the set of the frequency components within the frequency spectrum until a threshold condition is satisfied, thereby producing a final model; and generating the enhanced image from the final model of the volume of tissue.

11. The method of claim 10, wherein generating the initial model comprises generating a set of acoustomechanical parameter slices associated with a set of coronal slices through a volume of breast tissue, and wherein the method omits consideration of out-of-plane acoustic waveform scattering in modeling two dimensional wave propagation.

12. The method of claim 10, wherein generating the initial model comprises generating an initial sound speed model representing a distribution of sound speed across the region of the volume of tissue, and wherein generating the initial sound speed model is performed according to a travel time tomography algorithm with iteration until reduction of ray artifacts in the initial sound speed model satisfies an artifact threshold condition.

13. The method of claim 10, wherein extracting the set of frequency components from the set of acoustic signals includes: time windowing data derived from the set of acoustic waveforms, according to a travel time selection algorithm that identifies primary transmitted portions of the set of acoustic signals; and applying sinusoidal tapers to boundaries of time windowed data derived from the set of acoustic waveforms.

14. The method of claim 10, wherein extracting the set of frequency components from the set of acoustic signals includes: discarding waveforms of the set of acoustic signals associated with emitter-receiver pairs of the transducer outside of an arc of 270 degrees.

15. The method of claim 10, wherein performing the forward modeling process comprises modeling propagation of acoustic waves transmitted through the volume of tissue according to a Helmholtz operation expressed as:

$[\nabla^2 + \omega^2/c(r)^2]u(r,\omega) = s(r,\omega)$, where $\nabla^2$ is the Laplacian operator, and $[\nabla^2 + \omega^2/c(r)^2]$ is a Helmholtz operator, including $\omega$ as the first frequency component, c as the initial sound speed model, u as an expected numerical wavefield obtained at positions r of the transducer for the first frequency component $\omega$, and s is a spatial ultrasound source of the transducer.

16. The method of claim 10, wherein the set of acoustic signals are derived from acoustic waveforms transmitted through a plurality of two-dimensional imaging panes through the volume of tissue.

17. The method of claim 10, wherein generating the first simulated wavefield comprises generating the first simulated wavefield according to a forward modeling process.

18. The method of claim 10, further comprising rendering the enhanced image of the volume of tissue at a display in communication with the computing system, wherein rendering the enhanced image includes rendering an indication of at least one tissue mass observable in the enhanced image.

19. The method of claim 10, wherein generating the updated model includes generating the updated model based upon a solution to an inverse problem generated with the first simulated wavefield, wherein determining the solution to the inverse problem includes performing an iterative process that processes the initial model with a gradient of an error cost function, and wherein the gradient of the error cost function includes a component derived from the first simulated wavefield.

20. The method of claim 10, wherein iteratively refining the updated model with solutions to the inverse problem comprises performing multiple iterations at each of the set of frequency components in sequence, until a final frequency component of the set of frequency components is processed.

21. The method of claim 19, wherein generating the initial model comprises generating an initial attenuation model upon inclusion of an imaginary component to an initial sound speed model.

22. The method of claim 21, wherein iteratively refining the updated model comprises iteratively refining the imaginary component independently of real components, in generating a final attenuation model.

* * * * *

UNITED STATES PATENT AND TRADEMARK OFFICE
CERTIFICATE OF CORRECTION

| | |
|---|---|
| PATENT NO. | : 10,743,837 B2 |
| APPLICATION NO. | : 14/817470 |
| DATED | : August 18, 2020 |
| INVENTOR(S) | : Gursharan Singh Sandhu et al. |

It is certified that error appears in the above-identified patent and that said Letters Patent is hereby corrected as shown below:

In the Specification

In Column 1, Line 12, insert following header and paragraph:
--STATEMENT AS TO FEDERALLY SPONSORED RESEARCH
This invention was made with Government support under Grant R44CA171601 awarded by the National Institutes of Health (NIH) through the National Cancer Institute. The Government has certain rights in the invention.--

Signed and Sealed this
Thirtieth Day of July, 2024

Katherine Kelly Vidal
Director of the United States Patent and Trademark Office